United States Patent
Bergström et al.

(10) Patent No.: US 8,754,286 B2
(45) Date of Patent: Jun. 17, 2014

(54) SHAPED ABSORBENT ARTICLE

(75) Inventors: Maria Gustin Bergström, Hälsö (SE); Carin Håkansson, Billdal (SE); Paulina Halleröd, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 620 days.

(21) Appl. No.: 12/742,160

(22) PCT Filed: Nov. 20, 2007

(86) PCT No.: PCT/SE2007/050874
§ 371 (c)(1),
(2), (4) Date: May 10, 2010

(87) PCT Pub. No.: WO2009/067059
PCT Pub. Date: May 28, 2009

(65) Prior Publication Data
US 2010/0256586 A1 Oct. 7, 2010

(51) Int. Cl.
*A61F 13/15* (2006.01)
*A61F 13/534* (2006.01)
*A61F 13/45* (2006.01)

(52) U.S. Cl.
CPC ... *A61F 13/53409* (2013.01); *A61F 2013/4562* (2013.01); *A61F 2013/4568* (2013.01)
USPC ............ 604/378; 604/385.03; 604/385.201

(58) Field of Classification Search
CPC ............... A61F 2013/4543; A61F 2013/455; A61F 2013/4556; A61F 2013/4562; A61F 2013/4568; A61F 2013/4575; A61F 2013/4581; A61F 2013/530861; A61F 2013/530883; A61F 2013/53778; A61F 2013/53786; A61F 13/53409; A61F 13/53436; A61F 13/53418; A61F 13/53427
USPC ........ 604/378, 379, 385.01, 385.101, 385.19, 604/385.23, 385.27, 383, 385.201
See application file for complete search history.

(56) References Cited

U.S. PATENT DOCUMENTS 3,364,931 A 1/1968 Hirsch
3,994,299 A * 11/1976 Karami ...................... 604/366
(Continued)

FOREIGN PATENT DOCUMENTS

EP 0 450 541 A2 10/1991
EP 1 035 818 B1 4/2002
(Continued)

OTHER PUBLICATIONS

Supplemental European Search Report dated Jun. 24, 2011, issued in the corresponding European Application No. 07835457.8-2124.
(Continued)

*Primary Examiner* — Lynne Anderson
*Assistant Examiner* — Bradley Philips
(74) *Attorney, Agent, or Firm* — Buchanan Ingersoll & Rooney PC

(57) ABSTRACT

An absorbent core for an absorbent article includes an upper absorbent core and a lower absorbent core. An acquisition layer is located between the upper and said lower absorbent cores in the thickness (Z) direction of the core. The upper absorbent core includes an opening and fold indications. The relative dimensions and positioning of the core components allows it to adopt a double-bowl shape. Further, an absorbent article includes the absorbent core.

18 Claims, 8 Drawing Sheets

(56) References Cited

U.S. PATENT DOCUMENTS

| | | | |
|---|---|---|---|
| 4,840,692 A * | 6/1989 | Kamstrup-Larsen | 156/252 |
| 4,988,344 A * | 1/1991 | Reising et al. | 604/368 |
| 5,295,988 A * | 3/1994 | Muckenfuhs et al. | 604/385.02 |
| 5,382,246 A * | 1/1995 | Kawano | 604/385.24 |
| 5,451,442 A * | 9/1995 | Pieniak et al. | 428/54 |
| 5,575,785 A * | 11/1996 | Gryskiewicz et al. | 604/385.28 |
| 5,578,025 A * | 11/1996 | May | 604/385.31 |
| 5,613,961 A | 3/1997 | DiPalma et al. | |
| 5,752,946 A | 5/1998 | Boberg et al. | |
| 6,007,528 A | 12/1999 | Osborn, III | |
| 6,011,195 A | 1/2000 | Muhs et al. | |
| 6,114,597 A | 9/2000 | Romare | |
| 6,241,714 B1 | 6/2001 | Raidel et al. | |
| 6,613,955 B1 * | 9/2003 | Lindsay et al. | 604/378 |
| 7,156,830 B2 * | 1/2007 | Koyama et al. | 604/385.24 |
| 2002/0087136 A1 | 7/2002 | Widlund | |
| 2003/0149412 A1 | 8/2003 | Damaghi et al. | |
| 2004/0102752 A1 * | 5/2004 | Chen et al. | 604/378 |
| 2004/0127870 A1 | 7/2004 | DiPalma et al. | |
| 2004/0186448 A1 | 9/2004 | Misek et al. | |
| 2005/0055000 A1 * | 3/2005 | Ohnishi | 604/367 |
| 2005/0165375 A1 * | 7/2005 | Fernfors et al. | 604/378 |
| 2006/0069366 A1 * | 3/2006 | Cole | 604/378 |
| 2006/0264859 A1 * | 11/2006 | Tsuji et al. | 604/385.28 |
| 2007/0179469 A1 * | 8/2007 | Takahashi et al. | 604/385.101 |
| 2009/0088718 A1 * | 4/2009 | Toyoshima et al. | 604/385.23 |

FOREIGN PATENT DOCUMENTS

| | | |
|---|---|---|
| EP | 1 634 556 | 3/2006 |
| EP | 1 880 700 A1 | 1/2008 |
| GB | 2 095 561 A | 10/1982 |
| GB | 2 289 417 A | 11/1995 |
| GB | 2 289 419 A | 11/1995 |
| GB | 2 304 586 A | 3/1997 |
| SE | 520 411 C2 | 7/2003 |
| WO | WO 91/09582 A1 | 7/1991 |
| WO | WO 93/21879 | 11/1993 |
| WO | WO 97/17920 A1 | 5/1997 |
| WO | WO 98/16179 A1 | 4/1998 |
| WO | WO 98/17217 | 4/1998 |
| WO | WO 2007/069958 A1 | 6/2007 |

OTHER PUBLICATIONS

Office Action (Decision on Grant) dated Jul. 27, 2011, issued in the corresponding Russian Patent Application No. 2010125189, and an English Translation thereof.

International Search Report (PCT/ISA/210) for PCT/SE007/050874 dated Aug. 26, 2008.

Written Opinion (PCT/ISA/273) for PCT/SE007/050874 dated Aug. 26, 2008.

* cited by examiner

SHAPED ABSORBENT ARTICLE

TECHNICAL FIELD

The present invention relates to an absorbent core for an absorbent article which is capable of adopting a predetermined three-dimensional shape when subject to pressure in the width direction. The invention also relates to an absorbent article comprising said core.

BACKGROUND OF THE INVENTION

Disposable absorbent articles such as diapers, sanitary napkins, incontinence guards and panty liners are used to absorb and manage bodily exudates such as urine, menses or faces. They can be manufactured so as to adopt a particular shape in use. Such shaped articles can provide improved security against leakage, as their form matches that of the wearer when in use.

For example, WO 97/17920 and GB 2 289 419 describe disposable liquid-absorbent articles in which pre-stressed curved elastic members are applied across the absorbent body. The elastic members deform the article in use to form a basin-type shape.

GB 2 289 417 describes an absorbent article having elastic means extending along the entire length of the article which define an outwardly convex curved path on either side of the longitudinal axis, so that the article adopts a bowl shape in use. GB 2 095 561 describes a disposable diaper having elastic strips 34, 36. A portion of each elastic strip overlies, and is bonded to, the pad.

WO97/17920 describes an absorbent article (e.g. incontinence guard) which has two or more curved elastic members arranged so as to provide the article with a bowl-shape. SE 520 411 shows an absorbent article (e.g. incontinence guard) having elastic threads above the core and elastic threads in the seams. U.S. Pat. No. 5,295,988 illustrates an absorbent article which has elastic material located under both the core and the seams. U.S. Pat. No. 4,988,344 discloses an absorbent article with multiple layers.

Absorbent articles which adopt a particular shape in use may provide improved fit, yet may also have problems handling large amounts of bodily waste, or rapid insults of bodily waste. There remains a need for improved absorbent articles which are designed to adopt a particular shape in use, said shape being able to receive, distribute and store large amounts of bodily waste rapidly and effectively. It is also advantageous that such absorbent articles can be manufactured in a simple, adaptable, cost-effective way.

SUMMARY OF THE INVENTION

The invention provides an absorbent core for an absorbent article. The absorbent core extends in the length (Y), width (X) and thickness (Z) directions. The absorbent core comprises an upper absorbent core and a lower absorbent core. The upper core has an extension in the X-direction which is greater than that of the lower absorbent core in at least a region thereof.

An acquisition layer is located between said upper and said lower absorbent cores in the thickness (Z) direction, in at least said region, said acquisition layer having an extension in the X-direction which is less than that of the upper core in at least said region. The upper absorbent core comprises an opening located in at least said region, such that the opening in the upper absorbent core overlies both the acquisition layer and the lower absorbent core.

The upper core comprises fold indications which have their greatest extension substantially in the length direction (Y) and which are located between the opening and the edges of the upper core in the width direction (X) of the core.

The structure of the absorbent core allows it to adopt a "double-bowl" shape when subject to compression in the width (X) direction. The double-bowl shape is adopted at least in the region. This double-bowl shape is able to receive, distribute and store large amounts of bodily waste rapidly and effectively.

The opening in the upper core is suitably located in the centre of the upper core in the width (X) direction.

The absorbent core according to the invention may additionally comprise a resilient forming element which underlies at least the opening in the upper absorbent core. The forming element is preferably located between the acquisition layer and the lower absorbent core. At least in the said region, the forming element has an extension in the width (X) direction which is less than the extension in the width (X) direction of the upper absorbent core, and the extension in the width (X) direction of the lower absorbent core.

Applying pressure to the core in the width (X) direction causes it to adopt a double-bowl shape—a first bowl (A) which is defined by the curvature of the upper core and a second smaller bowl (B) contained within the first bowl (A) which is defined by the opening in the upper core.

The present invention also provides an absorbent article comprising the absorbent core of the invention, said absorbent article extending in the length (Y), width (X) and thickness (Z) directions. The absorbent article typically comprises a liquid-permeable topsheet and a liquid-impermeable backsheet. The liquid-permeable topsheet and liquid-impermeable backsheet may extend beyond the absorbent core in at least the width (X) direction and be joined to one another in the area outside the absorbent core to form an edge-seam.

The absorbent article may additionally comprise two elastic members, each elastic member having a major extension in the length (Y) direction of the article and a minor extension in the width (X) direction of the article. Each elastic member extends along one longitudinal edge of the upper absorbent core such that—along a major portion of the extension of the elastic members in the length (Y) direction—the elastic members overlie both the upper absorbent core and the edge-seam in the width (X) direction.

The elastic members can overlie both the upper absorbent core and the edge-seam in the width (X) direction along substantially their entire extension in the length (Y) direction. he elastic members are preferably located on the wearer-facing side of the upper core. The elastic members may overlie both the upper absorbent core and the edge-seam to a substantially equal extent in the width (X) direction.

Definitions

The term "upper", when used in reference to a component of the present invention is used to describe components which lie closer to the wearer's body when in use. Similarly, the term "lower" when used in reference to a component of the present invention is used to describe components which lie further from the wearer's body when in use.

Within the context of the present invention, the term "disposable" is used to describe an article which is not intended to be cleaned or reused, but is rather discarded after use.

BRIEF DESCRIPTION OF THE DRAWINGS

The invention will now be more closely described with reference to the enclosed Figures, in which.

DETAILED DESCRIPTION OF PREFERRED EMBODIMENTS

Figure 1:
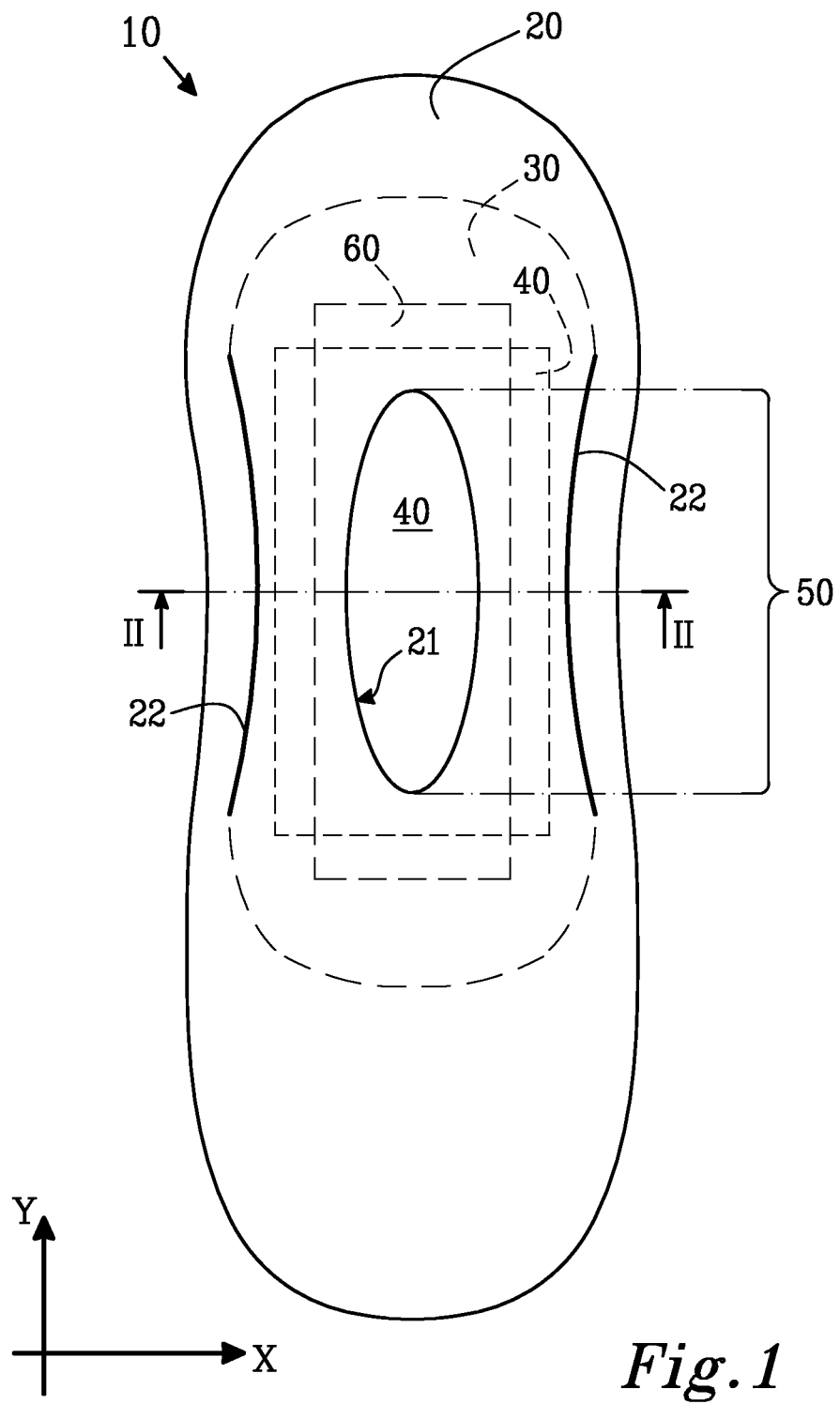
FIG. 1 is a plan view of an absorbent core according to the invention, seen from the upper core.

FIG. 1 shows an absorbent core 10 for an absorbent article 100. The absorbent core 10 is the component of the absorbent article 100 which receives and contains most liquid and other bodily exudates and can be of any conventional kind. As such, it typically comprises absorbent material. Examples of commonly-occurring absorbent materials are cellulosic fluff pulp, tissue layers, highly-absorbent polymers (so called superabsorbent polymers, SAP), absorbent foam materials, absorbent nonwoven materials or the like. It is common to combine cellulosic fluff pulp with superabsorbents in an absorbent body. It is also common to have absorbent cores comprising layers of different material with different properties with respect to liquid receiving capacity, liquid distribution capacity and storage capacity. The thin absorbent cores, which are common in for example baby diapers and incontinence guards, often comprise a compressed mixed or layered structure of cellulosic fluff pulp and superabsorbent. The size and absorbent capacity of the absorbent core 10 may be varied to be suited for different uses such as for infants or for incontinent adults.

Figure 4:
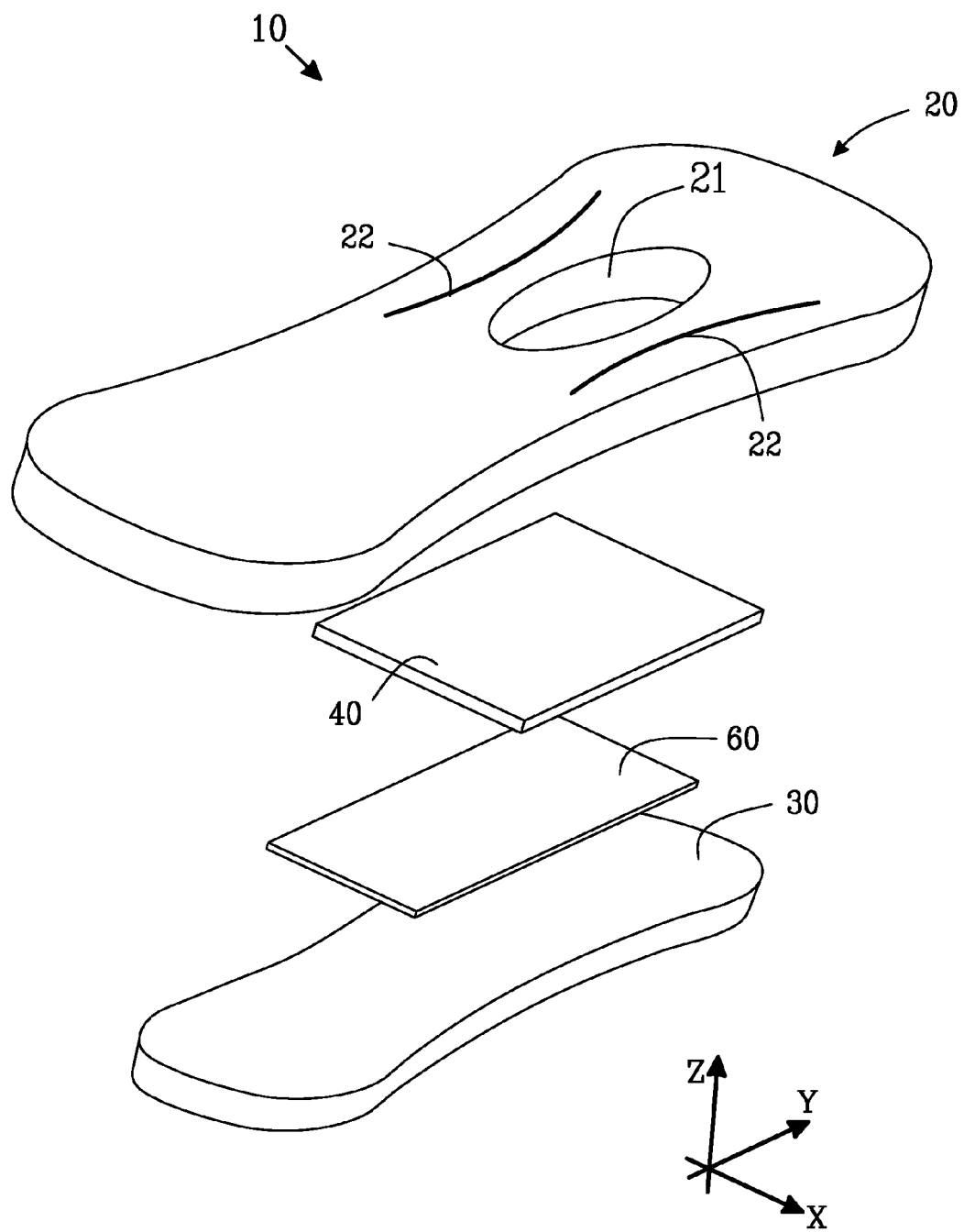
FIG. 4 is an exploded 3-D view of the absorbent core of FIG. 1.

The absorbent core 10 extends in the length (Y), width (X) and thickness (Z) directions, as shown in FIG. 4. Typically, the absorbent core 10 has a total length measured in a flat outstretched state of between 120 and 800 mm, a total width of between 40 and 250 mm and a total thickness of between 3 and 25 mm.

The absorbent core 10 has a layer structure comprising two cores—an upper absorbent core 20 located on the wearer-facing side of the absorbent core 10 and a lower absorbent core 30 located on the garment-facing side of the absorbent core 10. The upper and lower absorbent cores 20, 30 are separate entities, i.e. they are manufactured separately and placed on top of one another afterwards. The invention does not include unitary absorbent cores 10 in which certain regions or areas may be considered as being "upper" or "lower". The upper and lower cores 20, 30 may independently have any shape in the X-Y plane, such as oval, rectangular or hourglass-shaped. Each core preferably has a thickness in the Z-direction which tapers from the middle of the core towards the edges. The maximum thickness in the Z-direction of each of the upper core 20 and the lower core 30 suitably lies between 2 and 20 mm. The upper and lower cores 20, 30 typically comprise the absorbent material described above, which may be the same or different in the upper and lower cores. However, the lower core 30 usually has a higher absorbent capacity than the upper core 20, which can be achieved e.g. by using more superabsorbent polymer or more cellulosic fluff pulp.

In at least a region 50 of the length of the core 10, the upper core 20 has an extension in the X-direction which is greater than that of the lower absorbent core 30. Suitably, the upper absorbent core 20 is 1.2-3 times the width of the lower absorbent core 30, preferably 1.2-2.5 times and most preferably 1.2-2.0 times the width of the lower absorbent core 30 at a given point. The absorbent core 10 illustrated in FIG. 1 shows an upper core 20 with an extension in the X-direction which is greater than that of the lower core 30 over the entire length of the core 10—this is a preferred embodiment.

Indeed, the upper core 20 may even have an extension in both the X- and Y-directions which is greater than that of the lower core 30 (also shown in FIG. 1). However, it is essential for obtaining the required bowl form that—in at least a region 50 of the length of the core 10—the upper core 20 has an extension in the X-direction which is greater than that of the lower absorbent core 30.

The aforementioned region 50 defines an area extending primarily in the length direction (Y) in which the required double-bowl form is created when pressure is applied to the longitudinal edges of the upper absorbent core 20. The region 50 may extend over the entire length of the core 10 in the Y-direction. However, the region 50 may only extend over a portion of the extension of the core 10 in the length direction (Y), such as e.g. between 10% and 80%, preferably between 15% and 70%, more preferably between 20% and 50% of the extension of the core 10 in the Y-direction. Preferably, the region 50 is centred about a line extending in the width (X) direction which is located at one third of the length of the core 10.

An acquisition layer 40 is located between said upper 20 and said lower 30 absorbent cores in the thickness (Z) direction. The acquisition layer 40 acts to receive liquid rapidly, to temporarily hold it and to distribute it evenly to the upper and lower absorbent cores 20, 30. As such, it typically does not comprise any superabsorbent materials as described above, but suitably comprises fibrous materials, such as e.g. synthetic fibres.

The acquisition layer 40 is located in at least said region 50, and may be located along the entire length of the core 10. At least in region 50, the acquisition layer 40 has an extension in the X-direction which is less than that of the upper core 20. As shown in FIG. 1, the acquisition layer 40 may have an extension in the X-direction which is less than that of the upper core 20 over the entire length of the acquisition layer 40. The acquisition layer 40 may have any shape in the X-Y plane, such as oval, rectangular or hourglass-shaped. It preferably has a thickness in the Z-direction which is the same across the entire layer. The thickness of the acquisition layer 40 in the Z-direction is preferably between 0.5 and 7 mm.

The upper absorbent core 20 comprises an opening 21, as shown in FIGS. 1-8. The opening 21 extends through the entire thickness of the upper absorbent core 20, from one face to the other (see FIG. 4). The opening 21 may be introduced as part of the manufacturing process of the upper core 20, e.g. stamped or pressed out of the upper core 20, or formed in a mould as part of an airlaying process. The opening 21 is located in at least region 50, such that the opening 21 in the upper absorbent core 20 at least overlies both the acquisition layer 40 and the lower absorbent core 30. The opening 21 should have a surface area in the X-Y plane which is less than that of the lower absorbent core 30, and preferably has extensions in each of the X- and Y-directions which are less than those of the lower absorbent core 30.

To aid in the formation of the first bowl (A), the upper core 20 comprises fold indications 22 which have their greatest extension substantially in the length direction (Y) and which are located at least between the opening 21 and the edges of the upper core 20 in the width direction (X) of the core 10. These fold indications 22 provide extra flexibility in the upper core 20 (see FIGS. 3 and 8).

The fold indications 22 generally have their major extension in the length (Y) direction of the absorbent core 10. The upper core 20 preferably comprises at least two fold indications 22, one on either side of the opening 21, although more fold indications 22 may be included to provide even greater flexibility. The fold indications 22 have been illustrated in FIG. 1 as cuts which extend completely through the thickness of the upper core 20, however, compression lines, or cuts which do not extend completely through the upper core 20 may also be used as the fold indications 22. In addition, absorbent cores which comprise compressed airlaid material can have a lower material density airlaid at said fold indications 22, which becomes almost invisible upon compression. The fold indications 22 may extend to the edges of the upper absorbent core 20 in more than two places, so that the upper absorbent core 20 becomes divided into two or more separate portions which can move relative to one another. As shown in FIG. 1, the fold indications 22 may have a generally curved shape, and are closer to the axis of symmetry of the core 10 at the region 50 of the absorbent core 10.

It is advantageous, although not essential, as seen in FIGS. 2, 3, 6 7 and 8, that the lower absorbent core 30 has an extension in the width (X) direction which is similar to or the same as the distance between the fold indications 22 in the width (X) direction. Furthermore, it is advantageous if the fold indications 22 are located above the side edges of the lower absorbent core 30 along the length of the fold indications (when seen from the wearer-facing side of the product). In both these cases, the fold indications 22 and the lower absorbent core 30 can cooperate to best forming effect.

When compressed in the width (X) direction, the structure of the absorbent core 10 as described thus provides a particular double-bowl shape, particularly in the region 50. A first bowl (A) is defined by the curvature of the upper core 20 and a second smaller bowl (B) contained within the first bowl (A) which is defined by the opening 21 in the upper core 20 (see FIGS. 3 and 8). This double-bowl shape is particularly effective at receiving, distributing and storing large amounts of bodily waste rapidly and effectively. The location and overlie of the components of the absorbent core 10 allow the location, depth and form of the double-bowl form to be closely controlled, and to ensure that it forms in a predetermined way.

The region 50 of the core 10 may be seen as that region of the core 10 in which at least:
- the upper core 20 has an extension in the width (X) direction which is greater than that of the lower absorbent core 30;
- the acquisition layer 40 is located between the upper 20 and lower 30 absorbent cores;
- the acquisition layer 40 has an extension in the width (X) direction which is less than that of the upper core 20 and the opening 21 is at least partly located.

Fulfillment of these requirements causes the core 10 to adopt the required double-bowl form in the said region 50.

As the human body is symmetrical, the absorbent core is suitably symmetrical in the width (X) direction; i.e. it possesses an axis of symmetry running through its centre, parallel to the length (Y) direction. Absorbent cores 20, 30, acquisition layer 40, fold indications 22 and opening 21 are arranged symmetrically about this axis of symmetry.

Figure 2:
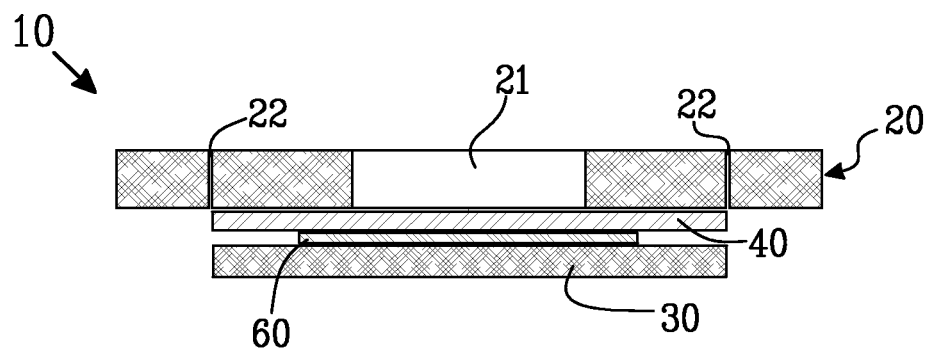
FIG. 2 is a cross-sectional view along the line II-II in FIG. 1 when the core is not compressed in the width direction X.
Figure 3:
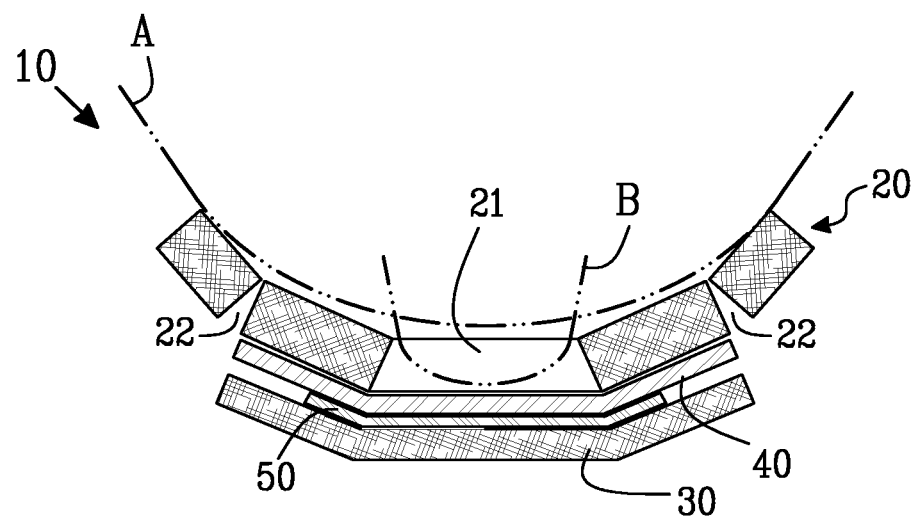
FIG. 3 is a cross-sectional view along the line II-II in FIG. 1 when the core is compressed in the width direction X.

To help prevent collapse of the three-dimensional structure of the absorbent core 10 under pressure in the width direction, the absorbent core 10 according to the invention may additionally comprise a resilient forming element 60 which underlies at least the opening 21 in the upper absorbent core 20. The forming element 60 is preferably located between the acquisition layer 40 and the lower absorbent core 30—in this way, it will be less noticeable to the wearer and will provide a better forming effect than if it were located elsewhere (FIG. 2). To maintain the required form in the core 10, the forming element 60 suitably has a width of between 13 and 20 mm, preferably between 14 and 19 mm, most preferably between 15.5 and 18 mm at a lateral compression of 25 N as measured according to the method described below. A forming element 60 with exhibiting high stiffness will be perceived as uncomfortable for the user. A stiff forming element 60 will also provide the absorbent article 100 with a relatively planar impact surface for urine.

Figure 5:
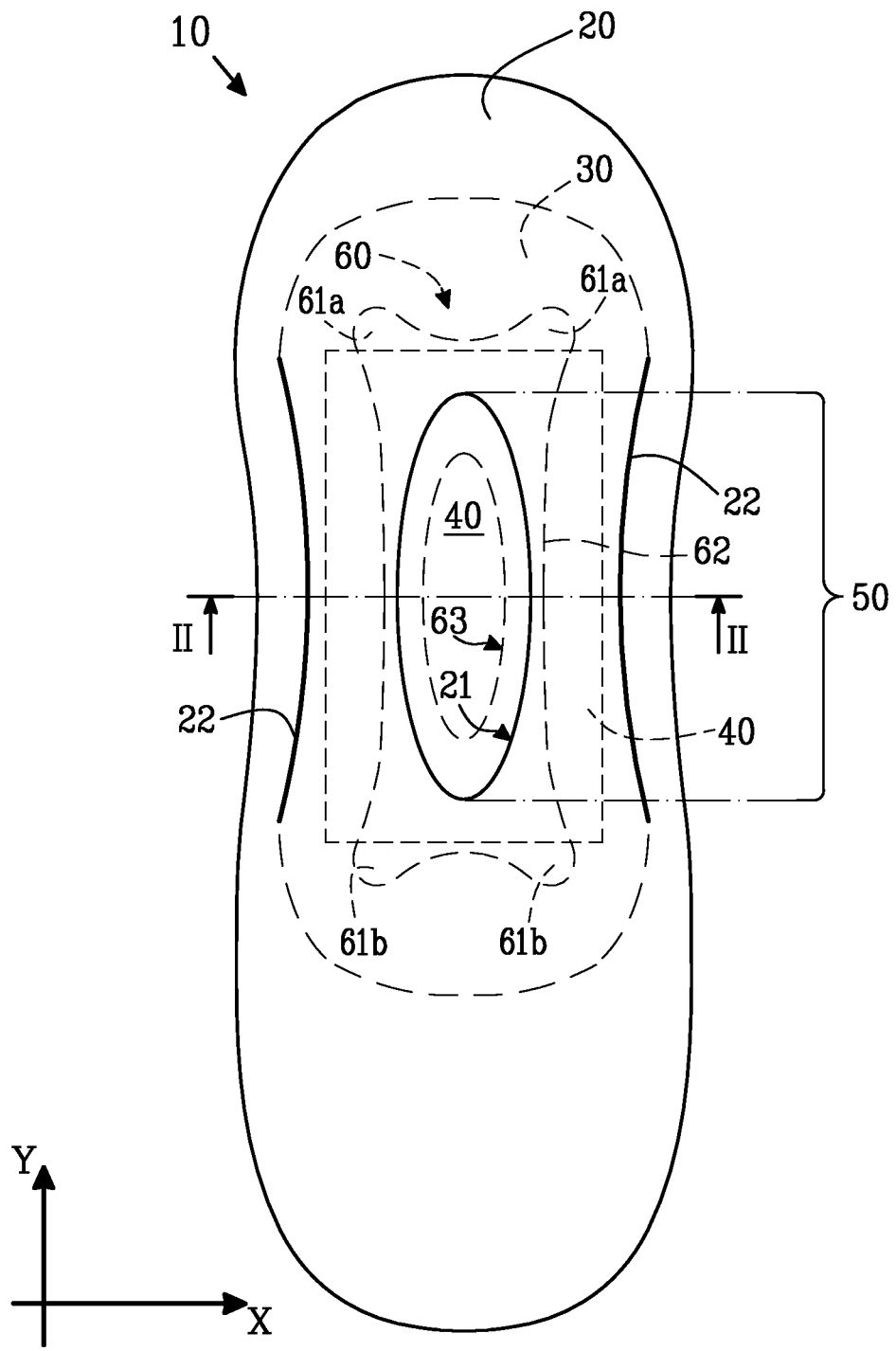
FIG. 5 shows an alternative embodiment of the forming element 60.

In a particular embodiment, the forming element 60 has a specific shape, as shown in FIG. 5. It has four legs 61: two front legs 61a extending forwards in the length (Y) direction and two back legs 61b extending backwards in the length (Y) direction. It has a narrowed waist 62, and a hole 63 in the middle. The narrowest portion 62 should be located between the tendons in the crotch region, where the distance between the wearer's legs is narrowest. The front legs 61a act to retain the form of the absorbent core 10 in the front of the core 10, while the back legs 61b have the same function in the rear of the core 10. The legs 61a, 61b also act to keep the core 10 in the optimal position with respect to the wearer's body, even when the wearer moves. In particular, the front legs 61a help prevent the article 100 moving backwards between the wearer's legs. The hole 63 should overlie the opening 21 in the upper core 20, to allow liquid transfer through to the lower core 30. The hole 63 also allows a certain flexibility in the transverse direction, which can be adjusted by changing the size and shape of the hole 63.

In said region 50, the forming element 60 preferably has an extension in the width (X) direction which is less than the extension in the width (X) direction of the upper absorbent core 20 and the extension in the width (X) direction of the lower absorbent core 30 (see FIG. 2). As the forming element 60 is typically liquid-impermeable, such an arrangement makes liquid flow around the edges of the forming element 60 in the width (X) direction, which makes best use of the upper and lower absorbent cores 20, 30 by distributing liquid at least in the width (X) direction. In addition, the forming element 60 may have an extension in the length (Y) direction which is less than the extensions of the upper and lower absorbent cores 20, 30 in this direction. Liquid flow towards the ends of the core 10 is thus promoted. The extension of the forming element 60 in the width (X) direction in said region 50 should typically be no more than 40 mm, preferably no more than 32 mm at its narrowest point.

Forming element 60 is suitably made of a non-absorbent material, so that its physical and mechanical properties are substantially unaffected by liquid. As mentioned above, it should also have the required stiffness properties. Therefore, suitable materials for the forming element 60 are plastic films, perforated plastic films and reinforced tissue or reinforced nonwoven materials. Combinations of such materials in laminate form are also possible.

All layers (upper core 20, acquisition layer 40, lower core 30 and optional forming element 60) are suitably in contact over substantially their entire area of overlap. They are preferably joined to one another in their area of overlap, through any suitable means known in the art, e.g. gluing, thermal welding or ultrasonic welding. Adhesive bonding may be e.g. pattern bonding or spiral bonding. Therefore, upon compression of the core in the width (X) direction, upper core 20, acquisition layer 40, lower core 30 and optional forming element 60 generally flex or bend as a single unit.

Figure 6:
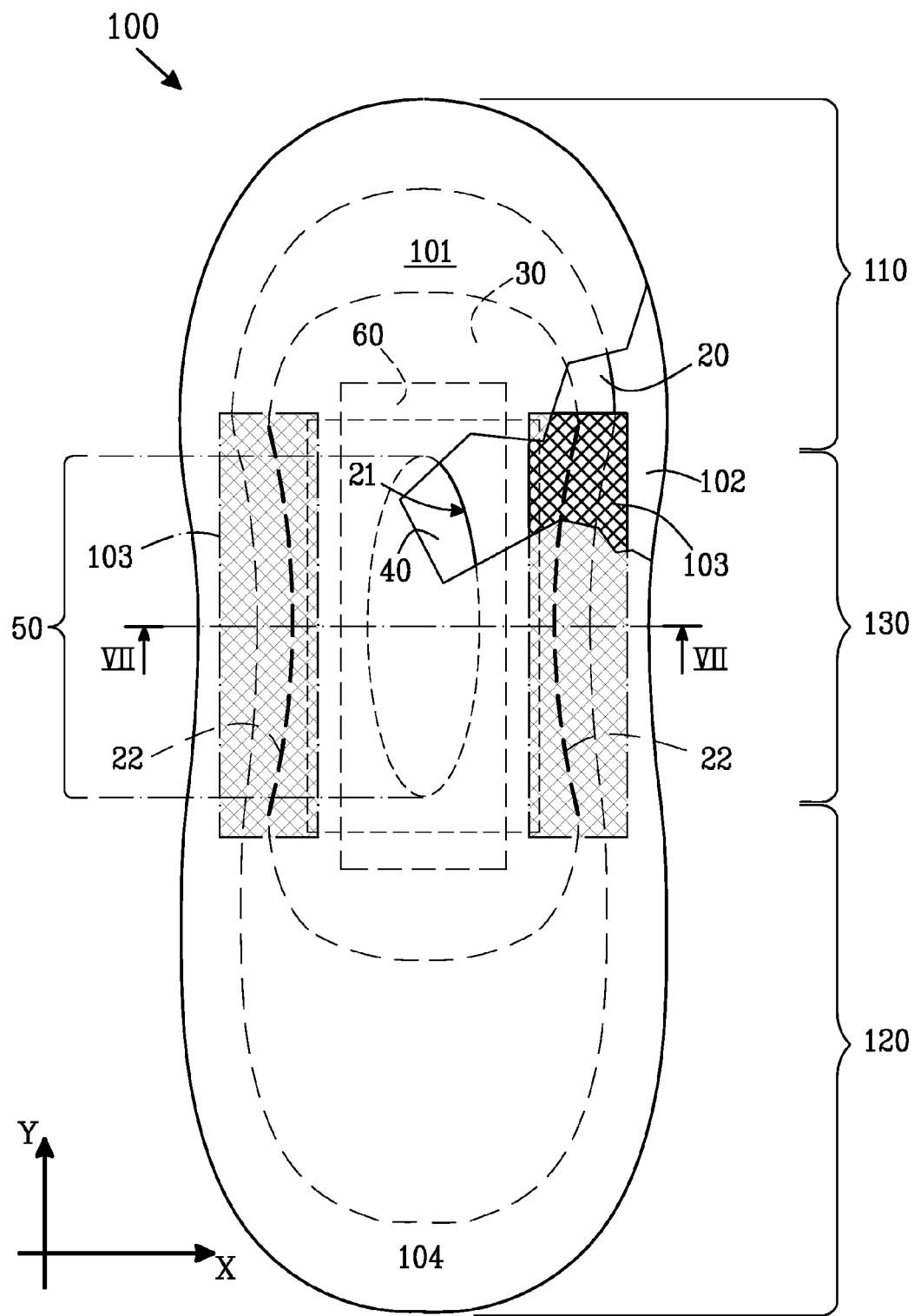
FIG. 6 is a plan view of an absorbent article comprising the absorbent core of the invention.

The invention also relates to an absorbent article 100 (illustrated in FIGS. 6-8) comprising an absorbent core 10 as described herein. The absorbent article 100 is disposable, in that it is not intended to be reused, but rather discarded after being soiled. FIG. 6 illustrates a light incontinence guard, although the invention is equally applicable to other absorbent articles such as diapers, sanitary napkins and panty liners. The absorbent article 100 has a front portion 110 which in use is intended to cover the user's pubic mound and face towards the user's stomach, a rear portion 120 which in use is intended to cover the user's buttocks and face towards their back, and a crotch portion 130 located between said front and rear portions 110, 120 in the length direction (Y) of the article 100.

In the same way as for the absorbent core 10, the absorbent article 100 extends in the length (Y), width (X) and thickness (Z) directions. It may comprise a liquid-permeable topsheet 101 and a liquid-impermeable backsheet 102, however articles are known which only comprise one of these components, or in which the absorbent core 10 is wrapped within a single sheet.

The topsheet 101 of the article 100 is the layer which lies in contact with the wearer's body when the article is in use. As such, it should be soft, non-irritating and comfortable against the skin, and bodily fluid should be able to pass through it without hindrance. The topsheet 101 can consist of a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet 101 may further be composed of tow fibres, which may be bonded to each other in a bonding pattern, as e.g. disclosed in EP-A-1 035 818. Further examples of materials suitable for topsheets are porous foams, apertured plastic films etc. The topsheet 101 may be different in different parts of the absorbent article 100.

The backsheet 102 of the article 100 is the layer which lies furthest from the wearer's body when the article is in use. To protect the wearer's garments from soiling, it should be liquid-impermeable, but is desirably gas-permeable to allow air and vapour to pass in and out of the article so that the warm, damp conditions which can arise in a diaper are reduced. Typically, the backsheet 102 is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. Examples of breathable backsheet materials are porous polymeric films, nonwoven laminates from spunbond and meltblown layers, laminates from porous polymeric films and nonwoven materials. The backsheet 102 may be different in different parts of the absorbent article 100. An improved appearance of the absorbent article may be achieved by using a textile backsheet.

Figure 7:
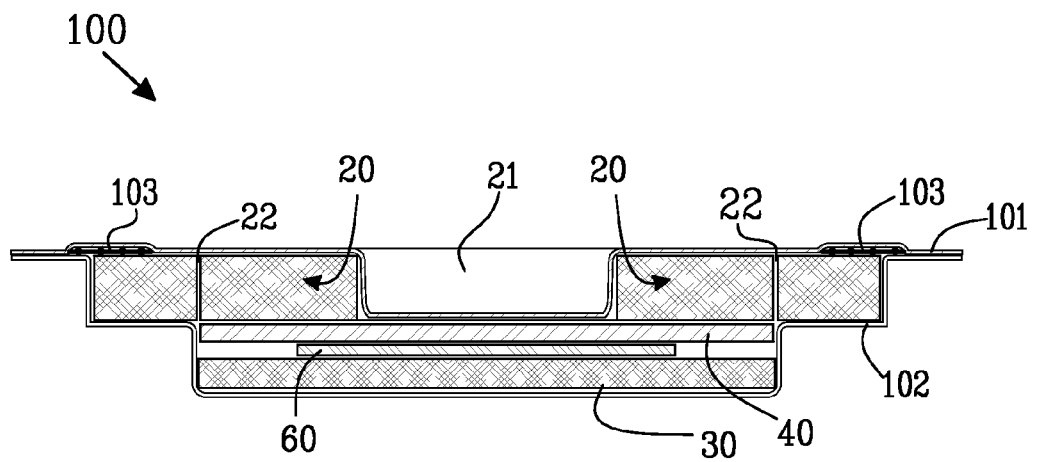
FIG. 7 is a cross-sectional view along the line V-V in FIG. 4 when the article is not compressed.
Figure 8:
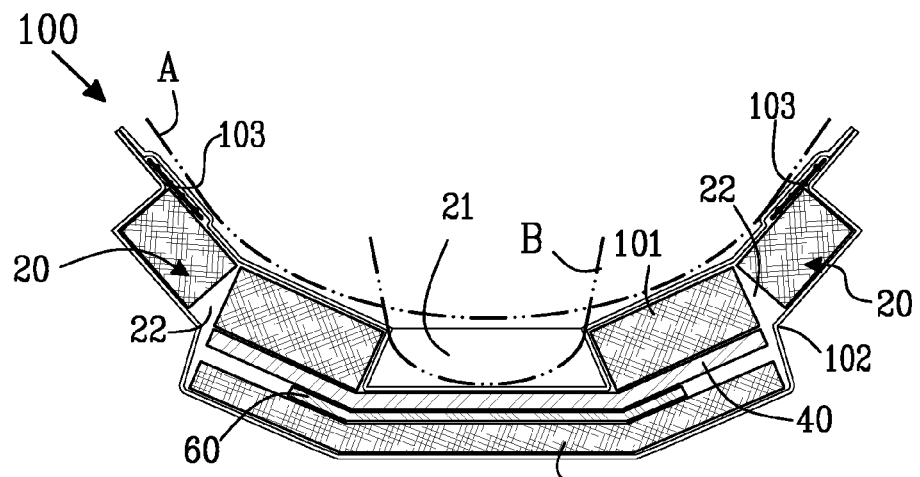
FIG. 8 is a cross-sectional view along the line V-V in FIG. 4 when the article is compressed in the width direction X.

The topsheet 101 and backsheet 102 generally have a similar extension in the plane of the article, while the absorbent core 10 has an extension which is somewhat smaller. The topsheet 101 and backsheet 102 are joined to one another around the periphery of the absorbent core 10, so that the core 10 is enclosed within the envelope formed by the topsheet 101 and the backsheet 102. In one embodiment, the fluid-permeable topsheet 101 and fluid-impermeable backsheet 102 extend beyond the absorbent core 10 in at least the width (X) direction and are joined to one another in the area outside the absorbent core 10 to form an edge-seam 104. The topsheet 101 and backsheet 102 may be joined to one another, and to the core 10, by any means common in the art, e.g. ultrasonic welding, thermal welding or gluing. Typically, the topsheet 101 is joined to the upper absorbent core 20 even within the opening 21, so that it makes contact with the acquisition layer 40 (as shown in FIG. 7). This provides a unitary appearance and function to the absorbent article 100.

The absorbent core 10 is located in the absorbent article 100 such that the bowls A and B are formed in the correct place—approximately one-third the length of the article 100 from the front edge (i.e. from that edge which, in use, is located nearest the wearer's stomach).

The absorbent article 100 according to the invention may comprise two elastic members 103 (FIGS. 6 & 7). Each elastic member 103 has a major extension in the length (Y) direction of the article 100 and a minor extension in the width (X) direction of the article 100. Each elastic member 103 extends along one longitudinal edge 22 of the upper absorbent core 20 such that—along a major portion of the extension of the elastic members 103 in the length (Y) direction—the elastic members 103 overlie both a portion of the upper absorbent core 20 and a portion of the edge-seam 104 in the width (X) direction. By "major portion" is meant that the elastic members 103 overlie both the upper absorbent core 20 and the edge-seam 104 in the width (X) direction over at least half their extension in the length (Y) direction, such as preferably at least 70% or at least 80% of their extension in the length (Y) direction. The elastic members 103 may even overlie both a portion of the upper absorbent core 20 and a portion of the edge-seam 104 in the width (X) direction along substantially their entire extension in the length (Y) direction. The elastic members 103, measured in a flat extended state, typically have an extension in the length (Y) direction of between 1 and 30 cm, preferably between 5 and 20 cm, more preferably between 8 and 18 cm, most preferably between 10 and 15 cm. Suitably, elastic members 103 are located adjacent the opening 21 in the width (X) direction and have an extension in the length (Y) direction of the article which is at least equal to that of the opening 21. To be able to overlie both a portion of the absorbent core 10 and a portion of the edge-seam 104, the elastic members 103 should also have a certain width when measured in a flat untensioned state, such as e.g. between 5 mm and 50 mm, preferably between 8 mm and 25 mm. The elastic members are unitary in at least the width (X) direction, and preferably in all directions (X, Y and Z); i.e. they should not comprise a plurality of elastic elements, some of which might overlie the absorbent core 10 and some of which might overlie the edge-seam 104.

Elastic members in articles of the prior art are typically located solely within the edge-seam. As the edge-seam is usually highly flexible, such an arrangement of elastics therefore has limited effect on the shape of the absorbent core, and only the edge-seam is pulled up by the elastic members. It is therefore common that the absorbent core remains relatively planar, and the bowl shape of the article is provided solely by the edge-seams.

In the present invention, however, elastic members 103 overlie (and are joined to) both a portion of the absorbent core and a portion of the edge-seam, which means that both these components are affected by the elastic members. Hence, the absorbent core 10 also adopts the advantageous double-bowl shape, leading to improved liquid-handling properties of the absorbent article 100 (see FIG. 8).

To obtain the best forming effect, the elastic members 103 are located on the wearer-facing side of the absorbent core 10. The elastic members 103 may overlie both a portion of the absorbent core 10 and a portion of the edge-seam 104 to a substantially equal extent in the width (X) direction (i.e. 50/50 overlap), although the overlap may be 60:40 or even 70:30 in one direction or the other. Preferably, the elastic members 103 overlie the absorbent core 10 more than they overlie the edge-seam. However, the elastic members 103 may even cover the entire edge seam 104 at each side edge of the article.

Method for Stiffness Determination

"Stiffness" in the present invention is measured as the width of an article at a lateral compression of 25 N. A Lloyd Instruments LRX apparatus (indicated generally as 200 in FIG. 9) is coupled to a computer 210 running Nexygen Ondio data collection software.

Absorbent articles 100 are stored at 20-23° C. and ca. 50% RH for 24 hours. The longitudinal centre line of the article is marked on the topsheet 101 of the absorbent article 100 with a soft marker pen, taking care not to damage the absorbent article. A mark is made along this longitudinal centre line at a distance which is a third of the length of the core 10 from the front edge of the core.

The apparatus consists of a clamp 201 arranged to hold the absorbent article of the invention in the vertical plane such that one long edge (side edge) of the article 100 faces upwards. The jaws of the clamp have product mark TG26, and are 10 cm long in the longitudinal (length) direction of the article.

Figure 9:
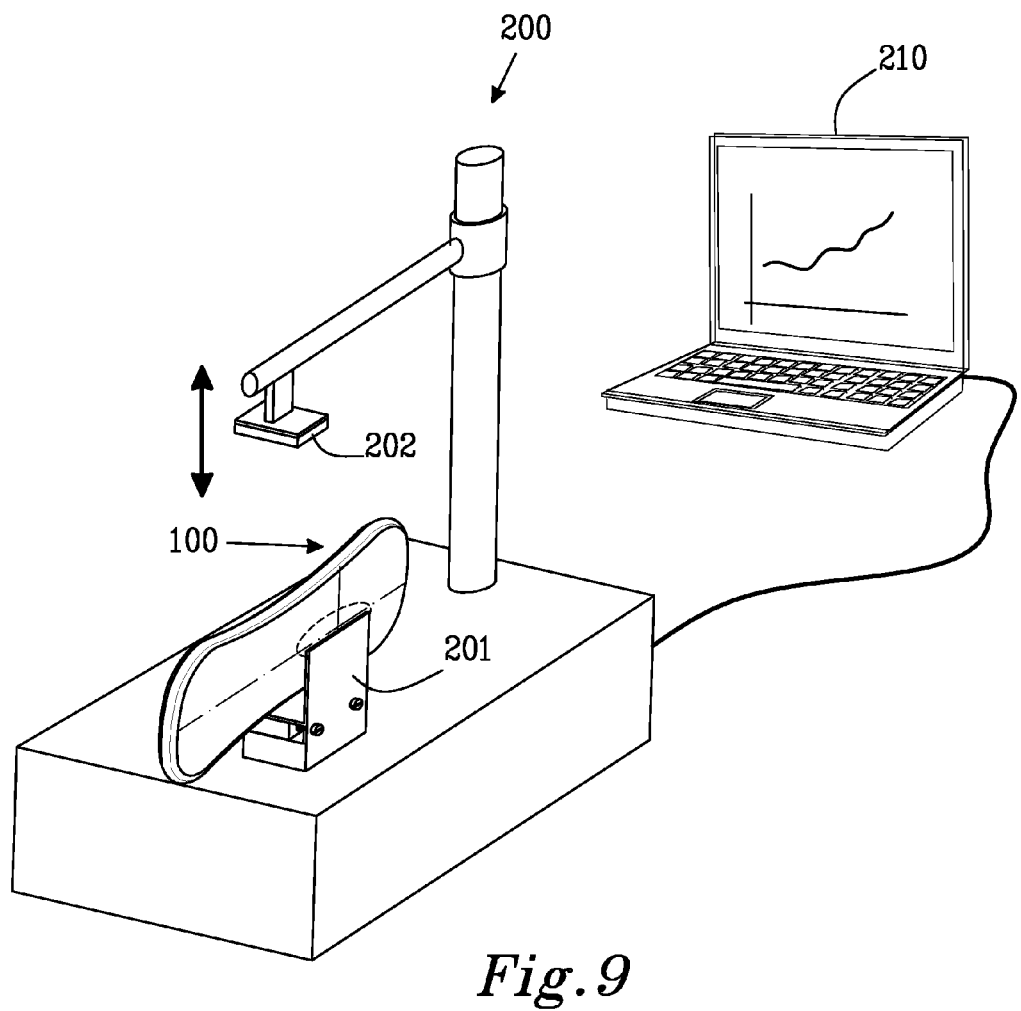
FIG. 9 shows an apparatus for measuring the stiffness of an absorbent article

The article 100 is clamped in the clamp 201 as shown in FIG. 9, such that the edges of the clamp jaws lie along the longitudinal centre line of the article, and so that the mark lying at ⅓ of the core length is placed centrally in the clamp (i.e. so that the jaws extend 5 cm in either direction along the longitudinal centre line about the mark). The jaws are closed about the article at a pressure of 1 kN.

A foot 202 is arranged vertically above the clamp. The foot 202 is a rectangular piece of metal, arranged in the horizontal plane, which is 3.5 cm long (in the same direction as the extension of the clamp jaws) and 4.8 cm wide. The centre of the foot 202 and the clamp 201 are aligned vertically above one another, and separated a sufficient distance that no contact is made between the foot 202 and the absorbent article 100. The apparatus is arranged so that the foot 202 moves vertically downwards at a pre-programmed rate (100 mm/minute is used in the present case).

The computer 210 is arranged so as to collect data relating to the downwards pressure exerted by the foot 202 and the distance between the foot 202 and the clamp 201. Of relevance in the present invention is the distance between the foot 202 and the jaws of the clamp 201 (i.e. the longitudinal centre line of the article 100) at a pressure of 25 N. Distances are measured from the bottom surface of the foot 202 to the upper surface of the clamp 201.

Figure 10:
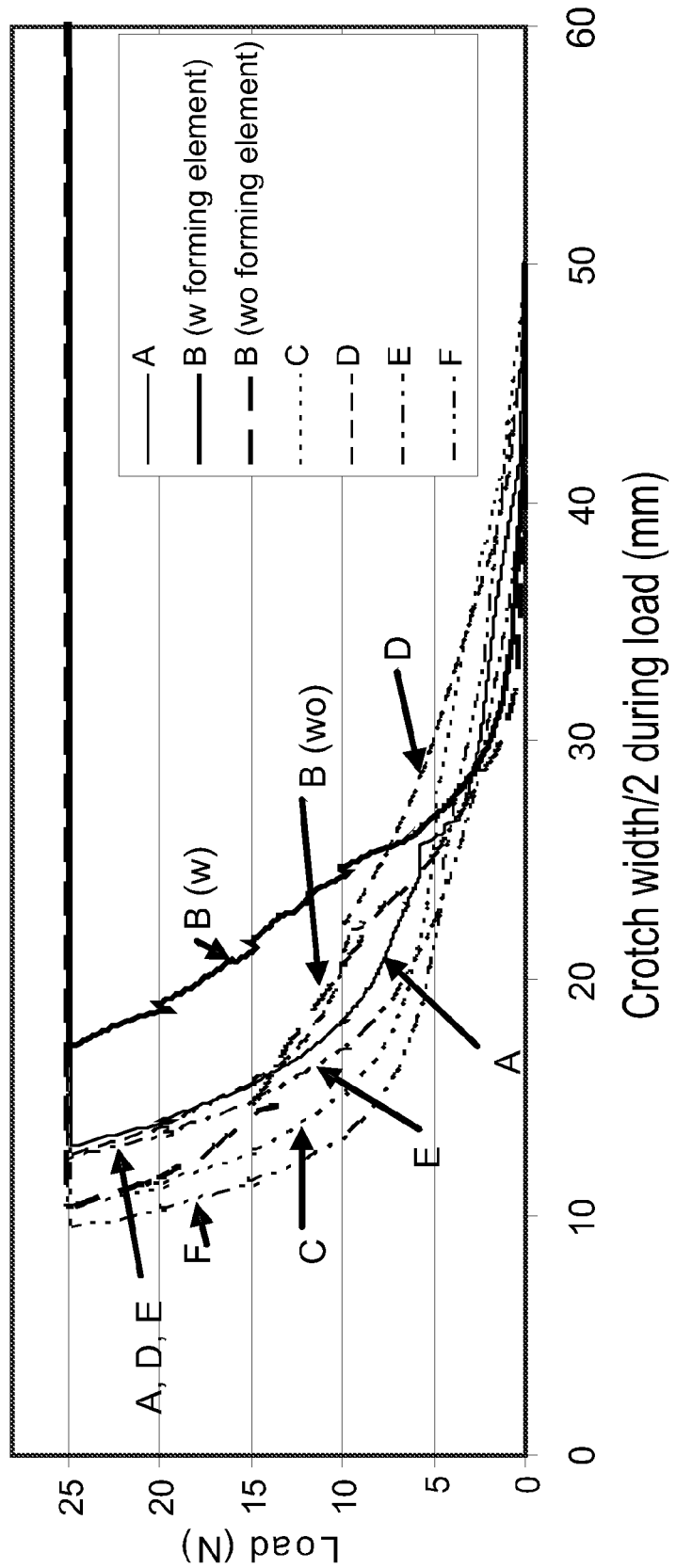
FIG. 10 is a plot showing stiffness measurements for various absorbent articles.

FIG. 10 is a plot of Load (N) versus the Crotch Width/2 during load (in mm) for a number of absorbent articles A-E. Products A, D and E have a thickness which is over 15 mm, while products B(w), B(wo), C and F have a thickness under 15 mm. Product B is tested with (w) and without (wo) a forming element.

When the products are laterally compressed with a force of ca. 10 N, the products with a forming element have a greater resistance to compression, and retain their crotch width better than products without a forming element. Above 15 N, there is a marked difference between products with and without forming elements in terms of maintaining crotch width and thereby obtaining a wider and flatter impact surface for liquid when it reaches the product.

It can also be seen in FIG. 10 that thin products (B(wo), C and F) have a lower residual crotch width than corresponding thick products (A, D, E) at a pressure of over 17 N.

When measuring the thickness of the absorbent article, use is made of a thickness gauge which has a rectangular good with dimensions of 40×100 mm. The foot exerts a pressure of 0.1 kPa on the article.

The thickness of two absorbent articles is measured, and the average value represents the thickness of the absorbent article. The articles have to be stored at 20-23° C. at ca.50% RH for 24 hours prior to the measurement. It is important that each article is flattened out before its thickness is measured, which can be done by firmly stretching the article.

The centre of the rectangular foot of the thickness gauge is position above the longitudinal centreline at a distance which is a third of the length of the core from the front edge of the core (i.e. the same longitudinal position on the article as the centre of the jaws are positioned when measuring the stiffness of the article). The longer sides (100 m) of the foot are arranged parallel to the longitudinal centrelines of the article to be measured. The foot is carefully lowered on the absorbent article and the thickness is read on the gauge after 5 seconds at a pressure of 0.1 kPa.

The present invention has been described with reference to a number of embodiments in the description and Figures. However, the invention should not be considered limited only to these embodiments, but rather features from different embodiments can be combined as desired. The scope of the invention should be considered as being defined in the appended claims.

The invention claimed is:

1. An absorbent core for an absorbent article, said absorbent core extending in length, width and thickness directions, and having a rear region, a crotch region and a front region in the length direction, said absorbent core comprising an upper absorbent core and a lower absorbent core, said upper absorbent core having an extension in the width direction which is greater than that of the lower absorbent core in at least the crotch region;
   an acquisition layer being located between said upper and said lower absorbent cores in the thickness direction, in at least said crotch region, said acquisition layer having an extension in the width direction which is less than that of the upper absorbent core in at least said crotch region;
   the upper absorbent core comprising an opening located in at least said crotch region, such that the opening in the upper absorbent core overlies both the acquisition layer and the lower absorbent core; a resilient forming element which underlies at least the opening in the upper absorbent core, wherein
   the upper absorbent core comprises fold indications which comprise a cut that extends at least partially through the upper absorbent core and have their greatest extension substantially in the length direction, and which are located at least between the opening and edges of the upper absorbent core in the width direction of the absorbent core, and the forming element is located between the acquisition layer and the lower absorbent core.

2. The absorbent core according to claim 1, wherein the opening in the upper absorbent core is located in the centre of the upper absorbent core in the width direction.

3. The absorbent article according to claim 1, wherein the fold indications have a curved shape, such that a portion of the fold indications that is closest to an axis of symmetry of the absorbent core is in said crotch region in the length direction of the absorbent core.

4. The absorbent core according to claim 1, wherein in at least said crotch region, the forming element has an extension in the width direction which is less than the extension in the width direction of the upper absorbent core, and the extension in the width direction of the lower absorbent core.

5. The absorbent core according to claim 1, wherein compression of the absorbent core in the width direction causes it to adopt a double-bowl shape—a first bowl which is defined by curvature of the upper absorbent core and a second smaller bowl contained within the first bowl which is defined by the opening in the upper absorbent core.

6. An absorbent article, comprising the absorbent core according to claim 1, said absorbent article extending in length, width and thickness directions.

7. The absorbent article according to claim 6, further comprising a liquid-permeable topsheet and a liquid-impermeable backsheet.

8. The absorbent article according to claim 7, wherein the liquid-permeable topsheet and the liquid-impermeable backsheet extend beyond the absorbent core in at least the width direction and are joined to one another in an area outside the absorbent core to form an edge-seam.

9. The absorbent article according to claim 8, further comprising two elastic members, each elastic member having a major extension in the length direction of the article and a minor extension in the width direction of the article, each elastic member extending along one longitudinal edge of the upper absorbent core such that—along a major portion of the extension of the elastic members in the length direction—the elastic members overlie both a portion of the upper absorbent core and a portion of the edge-seam in the width direction.

10. The absorbent article according to claim 9, wherein the elastic members overlie both a portion of the upper absorbent core and a portion of the edge-seam in the width direction along substantially the entire extension of the elastic members in the length direction.

11. The absorbent article according to claim 9, wherein the elastic members are located on a wearer-facing side of the upper absorbent core.

12. The absorbent article according to claim 9, wherein the elastic members overlie both a portion of the upper absorbent core and a portion of the edge-seam to a substantially equal extent in the width direction.

13. The absorbent article according to claim 2, wherein the fold indications have a curved shape, such that a portion of the fold indications that is closest to an axis of symmetry of the absorbent core is in said crotch region in the length direction of the absorbent core.

14. The absorbent article according to claim 1, wherein in at least said crotch region, the forming element has an extension in the width direction which is less than the extension in the width direction of the upper absorbent core, and the extension in the width direction of the lower absorbent core.

15. The absorbent article according to claim 10, wherein the elastic members are located on a wearer-facing side of the upper absorbent core.

16. The absorbent article according to claim 10, wherein the elastic members overlie both a portion of the upper absorbent core and a portion of the edge-seam to a substantially equal extent in the width direction.

17. The absorbent article according to claim 11, wherein the elastic members overlie both a portion of the upper absorbent core and a portion of the edge-seam to a substantially equal extent in the width direction.

18. An absorbent core for an absorbent article, said absorbent core extending in length, width and thickness directions, said absorbent core comprising an upper absorbent core and a lower absorbent core, said upper absorbent core having an extension in the width direction which is greater than that of the lower absorbent core a resilient forming element which underlies at least the opening in the upper absorbent core in at least a region thereof;
an acquisition layer being located between said upper and said lower absorbent cores in the thickness direction, in at least said region, said acquisition layer having an extension in the width direction which is less than that of the upper absorbent core in at least said region;
the upper absorbent core and the forming element is located between the acquisition layer and the lower absorbent core comprising one single opening only, located in at least said region, such that the opening in the upper absorbent core overlies both the acquisition layer and the lower absorbent core, wherein
the upper absorbent core comprises fold indications which comprise a cut that extends at least partially through the upper absorbent core and have their greatest extension substantially in the length direction, and which are located at least between the opening and edges of the upper absorbent core in the width direction of the absorbent core.

* * * * *